United States Patent [19]

Franz

[11] 4,106,923

[45] Aug. 15, 1978

[54] PHOSPHONOMETHYL GLYCINE ESTER ANHYDRIDES, HERBICIDAL COMPOSITION CONTAINING SAME AND USE THEREOF

[75] Inventor: John E. Franz, Crestwood, Mo.

[73] Assignee: Monsanto Company, St. Louis, Mo.

[21] Appl. No.: 701,766

[22] Filed: Jul. 2, 1976

Related U.S. Application Data

[60] Continuation-in-part of Ser. No. 630,392, Nov. 10, 1975, which is a continuation of Ser. No. 362,712, May 22, 1973, abandoned, which is a division of Ser. No. 170,388, Aug. 9, 1971, Pat. No. 3,799,758, which is a continuation-in-part of Ser. No. 123,057, Mar. 3, 1971, abandoned.

[51] Int. Cl.$^2$ ............................................. A01N 9/36
[52] U.S. Cl. ................................. 71/86; 560/171; 260/502.5
[58] Field of Search ............. 71/86; 260/482 R, 482 P

[56] References Cited

U.S. PATENT DOCUMENTS

| 3,160,632 | 12/1964 | Toy et al. ........................... 424/211 |
| 3,394,172 | 7/1968 | Schiefer ............................ 260/502.5 |
| 3,455,675 | 7/1969 | Irani ..................................... 71/86 |
| 3,556,762 | 1/1971 | Hamm ................................... 71/86 |
| 3,600,435 | 8/1971 | Randall et al. ........................ 71/86 |
| 3,799,758 | 3/1974 | Franz ................................... 71/86 |
| 3,832,396 | 8/1974 | Irani et al. ............................. 71/86 |
| 3,879,188 | 4/1975 | Fritz et al. ............................ 71/86 |

FOREIGN PATENT DOCUMENTS 3,922,735 10/1964 Japan .......................................... 71/86

OTHER PUBLICATIONS

Baird et al., "Introduction of a New Broadspectrum, etc.," (1971) CA77, No. 44234y, (1972).

*Primary Examiner*—Glennon H. Hollrah
*Attorney, Agent, or Firm*—Arnold H. Cole; Donald W. Peterson

[57] ABSTRACT

This disclosure contemplates N-phosphonomethyl glycine ester anhydrides as new compounds, as well as a process for producing such compounds. This disclosure also contemplates the use of such N-phosphonomethyl glycine ester anhydrides as herbicides and as aids in the harvesting of citrus fruit. Also disclosed are compositions containing the N-phosphonomethyl glycine ester anhydride as active ingredients, such composition being useful as herbicides and for aiding in the harvesting of citrus fruit.

30 Claims, No Drawings

PHOSPHONOMETHYL GLYCINE ESTER ANHYDRIDES, HERBICIDAL COMPOSITION CONTAINING SAME AND USE THEREOF

This application is a continuation-in-part of application Ser. No. 630,392 filed Nov. 10, 1975, which is a continuation of application Ser. No. 362,712 filed May 22, 1973, now abandoned, which is a division of Ser. No. 170,388 filed Aug. 9, 1971, now U.S. Pat. No. 3,799,758 which is a continuation-in-part of application Ser. No. 123,057 filed Mar. 10, 1971, now abandoned.

This invention relates to novel substituted aminomethyl phosphonic acid anhydrides, to herbicidal compositions containing same and to herbicidal method and methods of treating ripe citrus fruit employing such anhydrides.

The novel substituted amino methyl phosphonic acid anhydrides of this invention are those of the formula

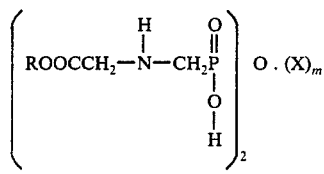

I.

wherein R is a member of the group consisting of alkyl groups containing from 1 to 12 carbon atoms, phenyl or phenoxy substituted lower alkyl groups when the alkyl group contains from 2 to 4 carbon atoms and $R'-O-C_nH_{2n}-$ groups where $n$ is an integer of from 2 to 4 and R' is a lower alkyl carbonyl group, X is water of hydration and $m$ is 0 or 1. Preferably the R group contains from 1 to 8 carbon atoms. Even more preferred the R group is an alkyl group containing from 1 to 4 carbon atoms or a substituted alkyl group containing up to 8 carbon atoms.

The alkyl groups represented by R are those containing from 1 to 12 carbon atoms and include, for example, methyl, ethyl, propyl, isopropyl, butyl, sec-butyl, isobutyl, hexyl, dodecyl groups and their isomers. The phenyl substituted lower alkyl groups are methyl, ethyl, propyl and butyl and the phenoxy substituted lower alkyl groups include ethyl, propyl and butyl. The lower alkyl groups represented by R' include for example, methyl, ethyl, propyl and butyl.

The compounds of this invention are produced by the reaction of an ester of N-phosphonomethyl glycine with thionyl chloride or an acyl chloride at ambient temperature. More particularly, the compounds of this invention are produced by forming an admixture of an ester of N-phosphonomethyl glycine of the formula

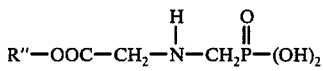

II.

wherein R" is a member of the group consisting of alkyl groups containing from 1 to 12 carbon atoms, phenyl or phenoxy substituted lower alkyl groups where the alkyl group contains from 2 to 4 carbon atoms and $H-O-C_nH_{2n}-$ groups where $n$ is an integer of from 2 to 4 and thionyl chloride or an acyl chloride of the formula

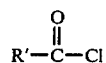

III.

wherein R' is a lower alkyl group and maintaining the admixture at a temperature sufficient to initiate and maintain the reaction whereby the substituted aminomethyl phosphonic acid anhydride of formula I is produced and then isolating said substituted aminomethyl phosphonic acid anhydride. The reaction is believed to take place in accordance with the following equation which for simplicity employs the ethyl ester of N-phosphonomethyl glycine and acetyl chloride.

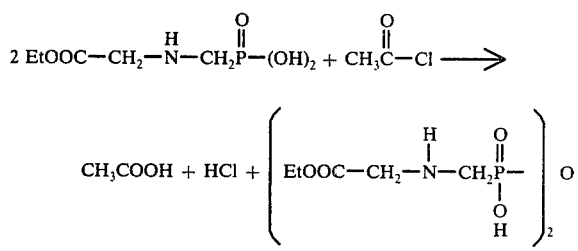

As can be seen by the above equation, when the only functional group to be reacted is the OH attached to phosphorus of the N-phosphonomethyl glycine compound, the molar ratio of the N-phosphonomethyl glycine compound to the acyl chloride theoretically is 2 to 1. Although lower ratios of the acyl halide to the N-phosphonomethyl glycine compound can be employed and some of the product anhydride will be produced, it will obviously be more difficult to recover the product. Even more preferred to insure completeness of reaction, one should employ an excess of the acyl halide inasmuch as the excess can be removed by volatilization prior to the recovery of the anhydride produced. It is therefore preferred to employ at least 2 moles of the acyl chloride for each hydroxyl group of the N-phosphonomethyl glycine compound to be reacted. For example, when a hydroxy substituted alkyl ester of N-phosphonomethyl glycine is employed, the ratio of acyl chloride to the glycine compound should be at least 4 to 1 and preferably is 10 to 20 to 1. It is therefore preferred to employ from 4 moles to 40 or more moles of the acyl halide for each mole of the N-phosphonomethyl glycine compound employed, the excess acyl chloride over that necessary to react with the reaction OH groups being recovered by distillation after the reaction is completed.

In the process of producing the compounds of the invention a solvent is not normally employed inasmuch as the excess acyl chloride reactant acts as the solvent. A solvent can be employed if desired. The solvent obviously should be anhydrous, one in which the reactants are soluble, and inert towards the N-phosphonomethyl glycine compound and the acyl chloride reactants. Such inert solvents are, for example, the halogenated hydrocarbons such as methylene chloride, ethyl chloride, chloroform, carbon tetrachloride, and the like.

The temperature at which the process of this invention is conducted can vary from 0° C. to 50° C. For reasons of economy and ease of reaction it is preferred to conduct the process of this invention at ambient temperatures, i.e., 18° to 30° C.

The process of this invention is normally conducted at atmospheric pressure. Although higher or lower pressures could be employed, no commensurate advantages are obtained thereby.

The compounds and compositions of this invention are useful as postemergent herbicides and as aids in the harvesting of citrus fruit.

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, ditertiary acetylenic glycols, polyoxyethylene derivatives of phenols and alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Fertilizers useful in combination with the active ingredients include for example ammonium nitrate, urea, potash, and superphosphate.

When operating in accordance with the present invention, effective amounts of the glycine compounds are applied to above-ground portions of plants. The application of liquid and particulate solid herbicidal compositions to above-ground portions of plants can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine compound employed. In foliar treatment for the control of vegetative growth, the active ingredients are applied in amounts from about 0.01 to about 50 or more pounds per acre. In applications for the control of aquatic plants, the active ingredients are applied in amounts of from about 0.01 parts per million to about 1000 parts per million, based on the aquatic medium. An effective amount for herbicidal control is that amount necessary for overall or selective control, i.e., a herbicidal amount. It is believed that one skilled in the art can readily determine from the teachings of this specification, including examples, the approximate application rate.

EXAMPLE 1

A mixture of 10 g. (0.05 mole) of ethyl N-phosphonomethyl glycinate and 25 mls. (27.5 g., 0.35 mole) of acetyl chloride produced a viscous gum which formed a granular solid after being stirred at room temperature for 20–30 minutes. The mixture was stored at room temperature for 16 hours and then was diluted with 50 mls. of ether. The white precipitate was collected and washed with ether until excess acetyl chloride was removed. The product was then washed with absolute ethanol and finally with ether. After being air-dried, the product was a white powder weighing 9.75 g. (95% yield), mp. 155–8 (dec). The infra-red spectrum indicated that the product was carbethoxymethylaminomethyl phosphonic anhydride hydrochloride.

The hydrochloride (2.1 g., 0.005 mole) prepared above and 20 mls. of 90% aqueous ethanol were stirred at room temperature for 75 minutes. The mixture was centrifuged and the residue washed with two 10 ml. portions of 90% aqueous ethanol. The product was finally washed with ether and dried at reduced pressure to yield 1–5 g. (76% yield) of white powder, mp. 185°–190° (dec). The infra-red spectrum of this product was identical to that of material previously prepared and identified as carbethoxymethylaminomethyl phosphonic anhydride hydrate which had the following analysis.

Calc'd. C, 30.46%; H, 6.14%; N, 7.11%; P, 15.71%.
Found C, 30.33%; H, 6.22%; N, 6.94%; P, 15.71%.
M.W. 394 — Found 377.

To a suspension of the hydrochloride (2.1 g., 0.005 mole) prepared above and 20 mls. of absolute ethanol was added 1.5 g. (0.025 mole) of propylene oxide. The mixture was stirred at room temperature for 75 minutes and then was centrifuged. The residue was washed with absolute ethanol and finally ether. The yield of air-dried white powder was 1.8 g. (95% yield), mp. 217-219 (dec). The infra-red spectrum indicated that the product was carbethoxymethylaminomethyl phosphonic anhydride. The same product was obtained when the corresponding hydrate, previously prepared using 90% aqueous ethanol, was washed with absolute ethanol.

EXAMPLE 2 n-Hexyl-N-phosphonomethyl glycinate (1.1 g., 0.0043 mole) was placed in a 50 ml. centrifuge tube and acetyl chloride (6.6 g., 0.084 moles) added to dissolve solid. The reaction mixture was then stoppered lightly and allowed to stand at room temperature (about 20°–25° C.) for approximately 3 hours, during which time a white solid precipitated. Ether (30 ml.) was added and the mixture centrifuged. The solid was washed with ether and air-dried. The solid was then washed with a small amount of water, tetrahydrofuran, then ethanol and finally diethyl ether. The white solid after air drying had a melting point of 238.5°–240° C. and was identified as $\alpha,\alpha'$-bis(hexyloxycarbonylmethylamino)methyl phosphonic acid anhydride and had the following analysis.

Calc'd. C, 44.26%; H, 7.84%; N, 5.74%; P, 12.68%.
Found C, 44,46%; H, 7.77%; N, 5.64%; P, 12.87%.

EXAMPLE 3

A mixture of 33.7 g. (0.10 mole) of n-dodecyl-N-phosphonomethyl glycinate and 120 mls. (132 g., 1.68 moles) of acetyl chloride was stirred at 25° overnight. The mixture was diluted with 200 mls. of ether and the precipitate collected. The product was washed with three 30 ml. portions of ether and was then slurried in 100 mls. of absolute ethanol. To the slurry was added 23.2 g. (0.40 mole) of propylene oxide. After stirring for 15 minutes at room temperature, the mixture was filtered. The residue was washed with six 30 ml. portions of ethanol and six 50 ml. portions of ether. The yield of air-dried waxy white powder was 15.5 g. (47% yield), mp. 222° (dec). The infra-red spectrum of this product was identical to that of material previously prepared and identified as $\alpha,\alpha'$-bis(dodecyloxycarbonylmethylamino)methyl phosphonic acid anhydride which had the following analysis.

Calc'd. C, 54.86%; H, 9.52%; N, 4.27%; P, 9.43%.
Found: C, 55.09%; H, 9.60%; N, 4.17%; P, 9.52%.

EXAMPLE 4 n-Octyloxy-N-phosphonomethyl glycinate (0.3 g., 0.0011 mole) was dissolved in acetyl chloride (5 ml.) and allowed to stand at ambient temperature overnight. A white precipitate formed, to which was added petroleum ether and the mixture centrifuged. The solid was triturated with tetrahydrofuran and air-dried. The solid was treated with a 50–50 volume mixture of ethanol and water, then ethanol and finally diethylether to yield a white powder (0.1 g. 0.000183 mole) identified as $\alpha,\alpha'$-bis(octyloxycarbonylmethylamino)methyl phosphonic acid anhydride having a melting point of 121.5°–126.5° C. (with decomposition) and the following analysis.

Calc'd.: C, 48.52%; H, 8.51%; N, 5.14%; P, 11.38%.
Found: C, 48.29%; H, 8.53%; N, 5.18%; P, 11.25%.

EXAMPLE 5 n-Butyl-N-phosphonomethyl glycinate (0.8 g., 0.0036 mole) was dissolved in acetyl chloride (10 ml.), lightly stoppered and allowed to stand overnight. During this period a white solid had precipitated. Diethyl ether (10 ml.) was added and the mixture centrifuged. The solid was washed with a 50–50 volume mixture of water and ethanol and centrifuged. The solid was then washed and centrifuged consecutively with ethanol and then diethyl ether, yielding a white solid (0.4 g., 0.000925 mole) having a melting point of 234°–237° C. with decomposition. This material was identified as $\alpha,\alpha'$-bis(butoxycarbonylmethylamino)methyl phosphonic acid anhydride and gave the following analysis.

Calc'd.: C, 38.89%; H, 6.99%; N, 6.48%; P, 14.33%.
Found: C, 38.86%; H, 7.10%; N, 6.46%; P, 14.17%.

EXAMPLE 6

To 3-hydroxypropyl-N-phosphonomethyl glycine (0.5 g., 0.0022 mole) was added acetylchloride (7 ml.) in a flask. The reaction mixture was stirred at room temperature (20°–25° C.). The solid became gummy and finally dissolved. The solution was allowed to stand at room temperature for 24 hours during which time a white solid precipitated. Diethyl ether was added and the mixture centrifuged. The white solid was washed consecutively with aqueous ethanol (50–50), ethanol (anhydrous) and then diethyl ether to give 0.35 g. (0.00067 mole) of a white powder identified as $\alpha,\alpha'$-bis(3-acetoxypropoxycarbonylmethylamino)methyl phosphonic acid anhydride

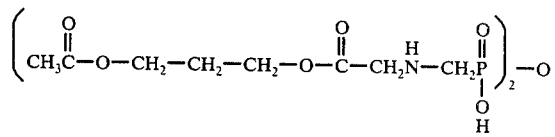

having a melting point of 213.5°–214.5° C. with decomposition and the following analysis.

Calc'd. C, 36.93%; H, 5.81%; N, 5.38%; P, 11.90%.
Found C, 36.80%; H, 5.92%; N, 5.26%; P, 12.00%.

EXAMPLE 7

$\beta$-phenylethyl-N-phosphonomethyl glycinate (.8 g., 0.003 mole) was charged into a 50 ml. round bottomed flask and acetyl chloride (10 ml.) added. The mixture was stirred at room temperature for 24 hours. The solid became waxy, then dissolved and a white solid precipitated. The solid was triturated with aqueous ethanol (50—50 volume mixture), then three times with anhydrous ethanol, and finally three times with ether to yield a white powder (0.6 g, 0.00114 mole) identified as $\alpha,\alpha'\lambda$ bis-($\beta$-phenylethyloxycarbonylmethylamino)methyl phosphonic acid anhydride, having a melting point of 240°–244° C. with decomposition and the following analysis.

Calc'd.: %C, 50.00; H, 5.72; N, 5.30; P, 11.72. Found: %C, 49.72; H, 5.69; N, 5.30; P, 11.59.

EXAMPLE 8

$\beta$-Phenoxyethyl-N-phosphonomethyl glycinate (0.8 g., 0.0028 mole) was charged into a 50 ml. round bottomed flask and acetyl chloride (10 ml.) added. The reaction mixture was stirred at room temperature. The solid became gummy and dissolved slowly and a white powder precipitated. After stirring at room temperature overnight, the solid was centrifuged from acetyl chloride and washed twice with ether. The solid was treated with excess propylene oxide in ethanol. After 15 minutes, the precipitate was collected, washed with ether and air-dried. A white solid weighing 0.450 g. (0.00080 mole) was identified as $\alpha,\alpha'$-bis(phenoxyethyleneoxycarbonylmethylamino)methyl phosphonic acid anhydride having a melting point of 206°–210° C. with decomposition and had the following analysis.

Calc'd.: %C, 47.15; H, 5.40; N, 5.00; P, 11.05. Found: %C, 47.27; H, 5.32; N, 5.03; P, 11.06.

EXAMPLE 9

Following the procedure of Example 8, isopropyl-N-phosphonomethyl glycinate (1.0 g., 0.0047 moles) was allowed to react with acetyl chloride (12 ml.) to yield $\alpha,\alpha'$-bis(isopropyloxycarbonylmethylamino)methyl phosphonic acid anhydride (.350 g., (0.00086 mole) which had a melting point of 207°–210° C. with decomposition and had the following analysis.

Calc'd.: %C, 35.65; H, 6.48; N, 6.93; P, 15.32. Found: %C, 35.48; H, 6.51; N, 6.74; P, 15.13.

EXAMPLE 10

The post-emergence herbicidal activity of various compounds of this invention is demonstrated as follows. The active ingredients are applied in spray form to 14 or 21 dayold specimens of various plant species. The spray, a water or organic solvent-water solution containing active ingredient and a surfactant (35 parts butylamine salt of dodecylbenzene-sulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded as indicated in the Table under column WAT (weeks after test). The data is given in Tables I and II, showing tests on different species of plants.

The post-emergence herbicidal activity index used in Tables I and II is as follows:

| Plant Response | Index |
| --- | --- |
| 0–24% Killed | 0 |
| 25–49% Killed | 1 |
| 50–74% Killed | 2 |
| 75–99% Killed | 3 |
| All Killed | 4 |
| Species not present at time of treatment | 5 |

The plants employed in the tests are as follows:

| | |
| --- | --- |
| A - Canada Thistle | K - Barnyard Grass |
| B - Cocklebur | L - Soybean |
| C - Velvet Leaf | M - Sugar Beet |
| D - Morning Glory | N - Wheat |
| E - Lambsquarters | O - Rice |
| F - Smartweed | P - Sorghum |
| G - Nutsedge | Q - Wild Buckwheat |
| H - Quackgrass | R - Hemp Sesbania |
| I - Johnson Grass | S - Panicum Spp |
| J - Downy Brome | T - Crabgrass |

TABLE I

| Compound from Example | WAT | kg/h | A | B | C | D | E | F | G | H | I | J | K |
| --- | --- | --- | --- | --- | --- | --- | --- | --- | --- | --- | --- | --- | --- |
| 1 | 2 | 4.48 | 3 | 3 | 3 | 2 | 2 | 5 | 2 | 4 | 4 | 2 | 4 |
| 1 | 4 |  | 4 | 3 | 4 | 2 | 3 | 5 | 3 | 4 | 4 | 3 | 4 |
| 2 | 4 | 11.2 | 0 | 1 | 3 | 2 | 3 | 2 | 1 | 3 | 1 | 2 | 3 |
| 4 | 4 | 11.2 | 0 | 1 | 1 | 2 | 1 | 1 | 0 | 2 | 0 | 0 | 0 |
| 5 | 4 | 11.2 | 4 | 3 | 3 | 3 | 4 | 2 | 3 | 4 | 3 | 3 | 4 |
| 6 | 4 | 4.48 | 3 | 4 | 4 | 3 | 4 | 4 | 3 | 4 | 3 | 4 | 4 |
| 7 | 4 | 4.48 | 3 | 5 | 3 | 3 | 4 | 3 | 3 | 4 | 3 | 3 | 4 |
| 8 | 4 | 4.48 | 2 | 3 | 3 | 2 | 4 | 3 | 3 | 3 | 3 | 0 | 3 |
| 9 | 4 | 4.48 | 2 | 3 | 3 | 3 | 4 | 4 | 3 | 3 | 4 | 2 | 4 |

TABLE II

| Compound from Example | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| 1 | 4 | 1.12 | 3 | 4 | 4 | 4 | 4 | 3 | 4 | 2 | 4 | 4 | 5 | 4 | 4 | 4 | 4 | 4 |
|  | 4 | .224 | 1 | 3 | 4 | 4 | 2 | 2 | 3 | 2 | 4 | 4 | 5 | 2 | 3 | 4 | 3 | 4 |
|  | 4 | .112 | 1 | 3 | 3 | 4 | 1 | 1 | 3 | 1 | 4 | 4 | 5 | 2 | 3 | 4 | 3 | 4 |
| 2 | 4 | 1.12 | 0 | 2 | 3 | 2 | 3 | 2 | 1 | 1 | 1 | 1 | 1 | 1 | 2 | 4 | 3 | 4 |
| 5 | 4 | 1.12 | 1 | 4 | 4 | 3 | 3 | 3 | 2 | 3 | 3 | 4 | 3 | 3 | 3 | 4 | 3 | 4 |
| 6 | 4 | 1.12 | 1 | 4 | 4 | 2 | 3 | 2 | 3 | 3 | 3 | 4 | 3 | 3 | 3 | 4 | 4 | 4 |
| 7 | 4 | 1.12 | 1 | 3 | 3 | 3 | 3 | 2 | 2 | 3 | 2 | 2 | 1 | 1 | 3 | 3 | 3 | 3 |
| 8 | 4 | 1.12 | 0 | 2 | 2 | 1 | 2 | 1 | 1 | 1 | 1 | 2 | 2 | 1 | 2 | 4 | 2 | 3 |
| 9 | 4 | 1.12 | 1 | 1 | 2 | 2 | 3 | 2 | 2 | 2 | 2 | 3 | 2 | 1 | 1 | 4 | 3 | 3 |

The following examples show the use of the compounds of this invention in a method for facilitating the harvest of fruit.

The compounds of this invention are most advantageously applied to the fruit-bearing plant by spraying.

While such application will normally be carried out with ground-based equipment, aerial spray techniques can be employed in those instances where a particular crop or cultural practices indicate economic feasibility.

For use in accordance with this invention, said compound may be formulated and applied as a liquid, a dust or a wettable powder following procedures known to the art. The active ingredient is admixed with a suitable inert material serving as a solvent, diluent or dispersant, after which such admixture is further diluted to a desired volume of spray. It will be understood that the composition to be applied can also contain surfactants, wetting agents, emulsifiers, sticking agents or other types of adjuvants whose nature and function have long been recognized in the art.

The method of this invention can be conveniently employed in the treatment of any fruit-bearing trees or plants. Representative of the fruits for which harvest can be thus facilitated are the common table fruit such as apples, plums and cherries, the citrus fruit such as oranges and lemons, along with others such as olives, grapes and nuts. It is particularly preferred to use the compound of the present invention as an aid in the harvesting procedures for the fruit of the non-deciduous trees, citrus and olives.

The time of application will vary from a few days (e.g., 3–4) up to about 2 weeks prior to the planned date of harvest. Specific selection within this short range will be dependent upon the type and variety of fruit being treated and upon the state of fruit development prior to treatment. These factors will also be considered in the determination of the rate of application. From a practical standpoint, the compounds of this invention are applied in a spray concentration of from about 100 to 4,000 ppm. (parts per million) active ingredient in total spray volume. A desirable degree of harvest facilitation is not obtained at lesser concentrations, while higher concentrations detract from economy and may also cause undesired injury to leaves and/or green fruit. Applications at concentrations of from 500 to 2,000 ppm. are particularly preferred.

To illustrate the practice of the method of this invention, tests are conducted to determine the effect of the compounds of this invention on various tree fruit. Branches selected for these tests are those which contain at least 20 pieces of fruit that are to be harvested within the following 2 weeks. The fruit are sprayed with a formulation of the active ingredient described herein, and a number of days after treatment, observations are made of the number of fruit which have fallen to the ground. A fruit which has not fallen is clipped from the branch with the stem attached to the fruit, and measurement is made of the force in pounds required to remove the fruit from the stem on a straight pull. Apparatus for such measurements is described in *Plant Physiology*, Volume 43, Part B, pages 1560–1576 (1968). When the force required to remove the fruit from the stem is too small to be measured on such apparatus, it is designated as "too loose to pull".

In these tests, observations are also made of any adverse effects on any leaves or green fruit which may be present on the branches. The extent of plugging, the removal of a part of the peel or rind when the stem is pulled from the fruit, is similarly noted along with any other indications of fruit injury. Although significant portions of most fruit crops are used for processing into juices, concentrates and canned sections, the remainder must be marketed as fresh fruit. While injuries such as rind pitting, burning or discoloration are not of real concern in the case of processed fruit, such undesirable changes in appearance are detrimental to fresh fruit sales. In addition, injuries such as plugging or rind splitting cannot be accepted for either market since they generally lead to rapid fruit rot.

In the illustrative tests hereinafter presented, it should be understood that untreated control branches are selected in each instance, and corresponding measurements and observations are made on the fruit thereof. The tests also included treatment of branches with cycloheximide, a known fruit abscission agent, at a rate which would normally cause all treated fruit to drop or be too loose for a measurement of pull force. By noting those instances in which this known compound does not demonstrate its expected activity, conclusions can be drawn as to the validity of a particular test due to the adverse effects of external factors. Some of these external factors include problems with the spraying apparatus which often leads to inadequate or non-uniform application, and rainfall within a few hours after application, which may wash off the chemical treatment.

EXAMPLE 11

Spray formulations for this test are prepared by mixing a small quantity (0.5 or 1 gram) of $\alpha,\alpha'$bis(ethoxycarbonylmethylamine)methyl phosphonic acid anhydride hydrate in acetone to a total volume of 100 or 200 ml. Then, 10 ml. of surfactant is added, followed by dilution with water to a total volume of 500 ml. The active ingredient in these formulations is thus present at concentrations of 500, 1,000 or 2,000 ppm., and sprays are applied to branches of Valencia oranges. After 7 days, fruit is removed from the test branches, and measurements of pull force are made for at least 10 fruit from each branch. At a concentration of 500 ppm, the fruit was too loose to pull. At 1000 and 2000 ppm., 99% of the fruit has fallen to the ground. None of treatments caused appreciable abscission of leaves or immature fruit drop. The untreated fruit on a control branch measured one day earlier had an average pull of 16.75 pounds and 40% plugging occurred.

EXAMPLE 12

In a second test conducted in accordance with Example 11, $\alpha,\alpha'$(ethoxycarbonylmethylamino)methyl phosphonic acid anhydride hydrate effected 95-100% mature fruit drop at 1000 and 2000 ppm. without causing any defoliation or immature fruit drop. There was no activity at 500 ppm., but there was an indication that a rainfall occurred 2-3 hours after chemical application inasmuch as a standard of this test cycloheximide was inactive. The untreated fruit on the control branch required an average pull of 19.00 pounds and 30 percent plugging occurs. Some leaf drop and fruit burn is noted at the higher rates.

In Examples 13 through 15 the same chemical is employed as in Example 11.

EXAMPLE 13

In this test, spray formulations were prepared as above at concentrations of 15.62, 31.25, 62.5, 125, 250, 500, 1000 and 2000 parts per million and branches containing Hamlin oranges were treated at each rate. After six days the untreated fruit require an average pull of 14.7 lbs. The following table gives the average pull on the sprayed fruit.

Table III

| Rate ppm. | Lbs. Pull |
|---|---|
| 15.6 | 7.6 |
| 31.25 | 5.1 |
| 62.5 | 7.5 |
| 125 | 5.1 |
| 250 | 2.4 |
| 500 | 3.4 |
| 1000 | 7.5 |
| 2000 | 5.0 |

The conditions of the branch in all of these tests was good. However, in all of the tests at rates above 15.6 ppm. severe fruit burn was noted, along with color enhancement of the oranges.

EXAMPLE 14

In this test spray formulations prepared as described in Example 12 with the same compound at a concentration of 500, 1000 and 2000 ppm. and two sets of branches containing Hamlin oranges sprayed at each rate and tested 7 days later. The untreated fruit had an average pull of 10.48 lbs. with 40% plugging. No plugging occurred with any of the treated fruit. All of the treated fruit were too loose to pull at all rates. There was no mature fruit burn, but mature leaf drop and mature fruit drop was noted.

EXAMPLE 15

In this test the compound employed in Example 12 was again tested on Hamlin oranges at 500, 1000 and 2000 ppm. After 7 days the untreated fruit had an average pull of 12.9 lbs. An average pull of 3.2, 1.7 and 1.1 was noted for the fruit treated with 500, 1000 and 2000 ppm. respectively.

In several other tests with Valencia or Hamlin variety of oranges improvements in the average pull force was noted.

What is claimed is:

1. A compound of the formula

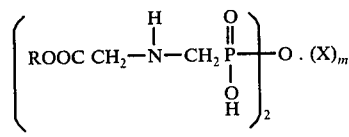

wherein R is a member of the group consisting of alkyl groups containing from 1 to 12 carbon atoms, phenyl or phenoxy substituted lower alkyl groups where the alkyl group contains from 2 to 4 carbon atoms and $R'-O-C_nH_{2n}-$ groups where $n$ is an integer of from 2 to 4 and $R'$ is a lower alkyl carbonyl group, X is water of hydration and $m$ is 0 or 1.

2. A compound of claim 1 wherein $m$ is 0.
3. A compound of claim 2 wherein R is an alkyl group of from 1 to 8 carbon atoms.
4. A compound of claim 2 wherein R is a phenoxyalkyl group.
5. A compound of claim 2 wherein R is a phenyl substituted alkyl group.
6. A compound of claim 1 which is α,α'bis(carbethoxymethylamino)methyl phosphonic acid anhydride hydrate.
7. A compound of claim 2 which is α,α'-bis(3-acetoxypropoxycarbonylmethylamino)methyl phosphonic acid anhydride.
8. A compound of claim 5 which is α,α'-bis-(phenylethoxycarbonylmethylamino)methyl phosphonic acid anhydride.
9. A compound of claim 4 which is α,α'-bis-(phenoxyethyleneoxycarbonylmethylamino)methyl phosphonic acid anhydride.
10. A compound of claim 3 which is α,α'-bis(isopropyloxycarbonylmethylamino)methyl phosphonic acid anhydride.
11. A herbicidal composition containing an inert diluent and a herbicidally effective amount of a compound of the formula

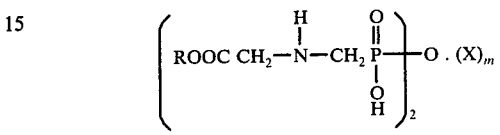

wherein R is a member of the group consisting of alkyl groups containing from 1 to 12 carbon atoms, phenyl or phenoxy substituted lower alkyl groups where the alkyl group contains from 2 to 4 carbon atoms and $R'-O-C_nH_{2n}-$ groups where $n$ is an integer of from 2 to 4 and $R'$ is a lower alkyl carbonyl group, X is water of hydration and $m$ is 0 or 1.

12. A composition of claim 11 wherein $m$ is 0.
13. A composition of claim 12 wherein R is an alkyl group of from 1 to 8 carbon atoms.
14. A composition of claim 12 wherein R is a phenoxyalkyl group.
15. A composition of claim 12 wherein R is a phenyl substituted alkyl group.
16. A composition of claim 11 wherein the compound is α,α'-bis(carbethoxymethylamino)methyl phosphonic acid anhydride hydrate.
17. A composition of claim 12 wherein the compound is α,α'-bis(3-acetoxypropoxycarbonylmethylamino)methyl phosphonic acid anhydride.
18. A composition of claim 15 wherein the compound is α,α'-bis(phenylethyloxycarbonylmethylamino)methyl phosphonic acid anhydride.
19. A herbicidal composition of claim 14 wherein the compound is α,α'-bis(phenoxyethyleneoxycarbonylmethylamino) methyl phosphonic acid anhydride.
20. A herbicidal composition of claim 13 wherein the compound is α,α'-bis(isopropyloxycarbonylmethylamino)methyl phosphonic acid anhydride.
21. A herbicidal method which comprises applying to plants a herbicidally effective amount of a compound of claim 1.
22. A herbicidal method which comprises applying to plants a herbicidally effective amount of a compound of claim 2.
23. A herbicidal method which comprises applying to plants a herbicidally effective amount of a compound of claim 3.
24. A herbicidal method which comprises applying to plants a herbicidally effective amount of a compound of claim 4.
25. A herbicidal method which comprises applying to plants a herbicidally effective amount of a compound of claim 5.
26. A herbicidal method which comprises applying to plants a herbicidally effective amount of a compound of claim 6.

27. A herbicidal method which comprises applying to plants a herbicidally effective amount of a compound of claim 7.

28. A herbicidal method which comprises applying to plants a herbicidally effective amount of a compound of claim 8.

29. A herbicidal method which comprises applying to plants a herbicidally effective amount of a compound of claim 9.

30. A herbicidal method which comprises applying to plants a herbicidally effective amount of a compound of claim 10.

* * * * *